(12) United States Patent
Bhalla et al.

(10) Patent No.: US 9,125,954 B2
(45) Date of Patent: Sep. 8, 2015

(54) METHOD FOR THE SYNTHESIS OF $^{18}$F-LABELLED BIOMOLECULES

(71) Applicant: GE HEALTHCARE LIMITED, Buckinghamshire (GB)

(72) Inventors: Rajiv Bhalla, St. Lucia Brisbane (AU); Anthony Wilson, Waddesdon (GB); Imtiaz Khan, Amersham (GB); Janne Brown, Amersham (GB)

(73) Assignee: GE Healthcare Limited, Buckinghamshire (GB)

( * ) Notice: Subject to any disclaimer, the term of this patent is extended or adjusted under 35 U.S.C. 154(b) by 0 days.

(21) Appl. No.: 14/351,625

(22) PCT Filed: Oct. 15, 2012

(86) PCT No.: PCT/EP2012/070400
§ 371 (c)(1),
(2) Date: Apr. 14, 2014

(87) PCT Pub. No.: WO2013/053940
PCT Pub. Date: Apr. 18, 2013

(65) Prior Publication Data
US 2014/0235861 A1 Aug. 21, 2014

Related U.S. Application Data

(60) Provisional application No. 61/547,088, filed on Oct. 14, 2011.

(30) Foreign Application Priority Data

Oct. 14, 2011 (GB) .................................. 1117786.2

(51) Int. Cl.
*C07C 227/16* (2006.01)
*A61K 51/04* (2006.01)
*C07B 59/00* (2006.01)
*C07C 319/14* (2006.01)
*C07C 303/30* (2006.01)
*C07D 451/02* (2006.01)
*C07C 67/10* (2006.01)

(52) U.S. Cl.
CPC .......... *A61K 51/0406* (2013.01); *A61K 51/0448* (2013.01); *A61K 51/0455* (2013.01); *C07B 59/001* (2013.01); *C07C 67/10* (2013.01); *C07C 227/16* (2013.01); *C07C 303/30* (2013.01); *C07C 319/14* (2013.01); *C07D 451/02* (2013.01); *C07B 2200/05* (2013.01)

(58) Field of Classification Search
CPC .......... A61K 51/0406; A61K 51/0455; A61K 51/04; A61K 51/0448; C07C 57/10; C07C 303/30; C07C 227/16; C07C 319/14; C07B 59/001; C07B 2200/05; C07D 451/02
USPC .................. 564/132, 238; 562/445; 546/132; 422/187
See application file for complete search history.

(56) References Cited

U.S. PATENT DOCUMENTS

| | | | |
|---|---|---|---|
| 8,058,311 B2 * | 11/2011 | Robins et al. | .................. 514/634 |
| 2005/0123475 A1 | 6/2005 | Lim | |
| 2010/0113763 A1 | 5/2010 | Moon et al. | |
| 2010/0143252 A1 | 6/2010 | Robins et al. | |

OTHER PUBLICATIONS

Zhang Applied Radiation and Isotopes, vol. 57, No. 3, Sept. 1, 2002 pp. 335-342.
Wilson, et.al. Applied Radiation and Isotpes, vol. 46 No. 8, Aug. 1, 1995 p. 766.
Mingwei, et.al. Journal of Radioanalytical and Nuclear Chemistry, vol. 270, No. 2, Nov. 1, 2006 pp. 439-443.
Lundkvist, et.al. Nuclear Medicine and Biology, vol. 24, No. 7 Oct. 1, 1997 p. 622.
Sang, et.al. European Journal of Nuclear Medicine and Molecular Imaging, vol. 34, No. 9, Mar. 24, 2007 pp. 1406-1409.
Robins, et.al. Bioorganic and Medicinal Chemistry Letters, vol. 20, No. 5, 2010, pp. 1749-1751.
Wang, et.al. Journal of Radioanalytical and Nuclear Chemistry, vol. 270, No. 2, pp. 439-443, 2006.
Lundkvist, et.al. Nuclear Medicine and Biology, vol. 24, 1997 pp. 621-627.
Chaly, et.al. Applied Radiation and Isotopes vol. 51, 1999 pp. 299-305.
PCT/EP2012/070400 ISRWO Dated Jan. 25, 2013.
GB1117786.2 Search Report Dated Feb. 20, 2012.

\* cited by examiner

*Primary Examiner* — Shailendra Kumar
(74) *Attorney, Agent, or Firm* — Parks Wood LLC; Collen A. Beard, Esq.

(57) ABSTRACT

The present invention provides a method for the synthesis of $^{18}$F-labelled biomolecules, which is amenable to automation. The present invention also provides a cassette for automating the method of the invention. The method of the present invention provides numerous advantages over the prior art methods. One less purification step is required as compared with known methods. Also, one less reagent is required as a particular reagent is employed in two different steps. The chemistry process is thereby simplified, the cost of goods is reduced and the burden of validation and documentation of reagents required for GMP clinical production is minimized.

21 Claims, 2 Drawing Sheets

METHOD FOR THE SYNTHESIS OF 18F-LABELLED BIOMOLECULES

Figure 1:
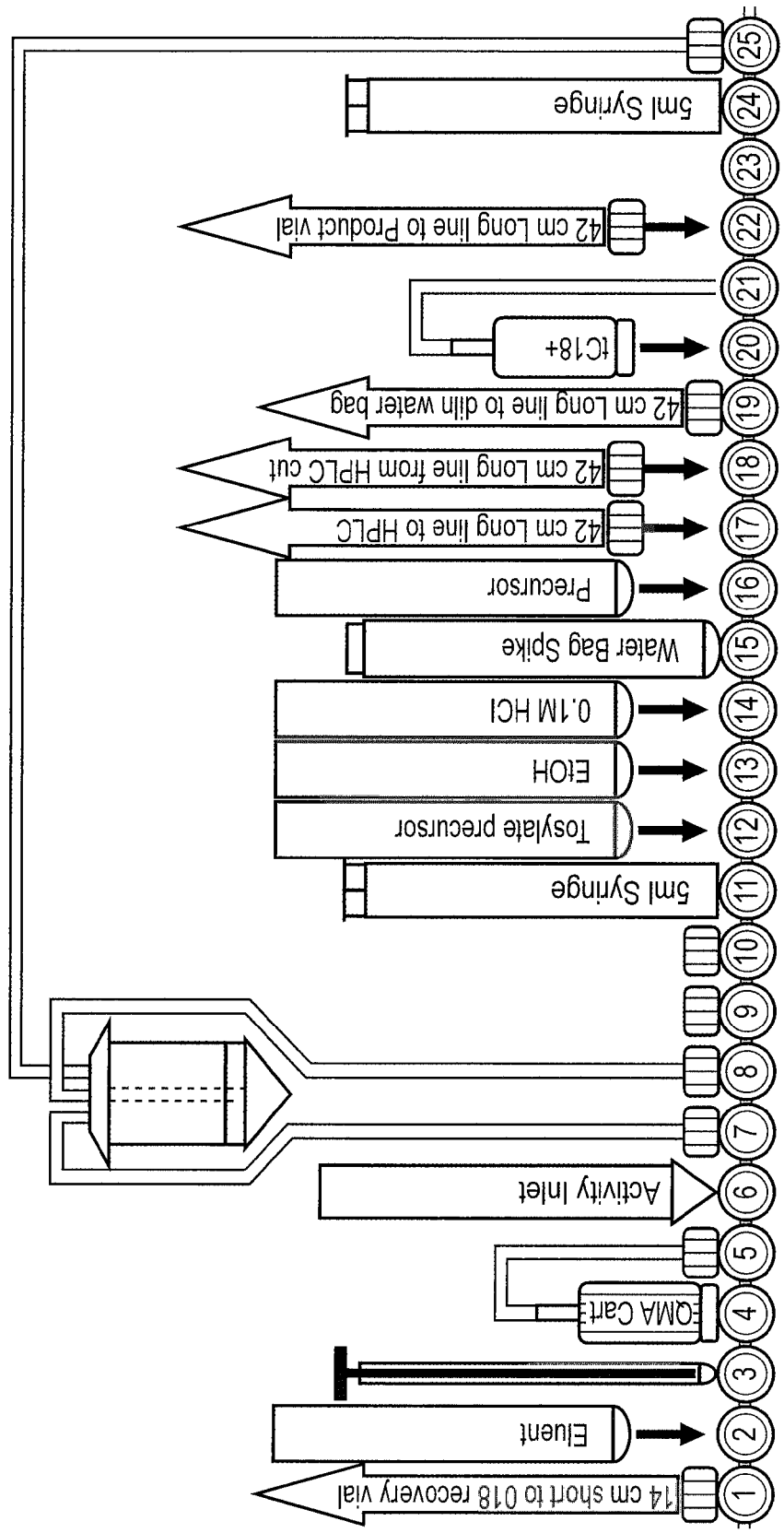

This application is a filing under 35 U.S.C. 371 of international application number PCT/EP2012/070400, filed Oct. 15, 2012, which claims priority to Great Britain application number 1117786.2 filed Oct. 14, 2011 and to U.S. application No. 61/547,088 filed Oct. 14, 2011, the entire disclosure of which is hereby incorporated by reference.

TECHNICAL FIELD OF THE INVENTION

The present invention relates to the field of radiopharmaceuticals, and in particular to the preparation of compounds suitable for use in positron emission tomography (PET). A method for the synthesis of compounds labelled with $^{18}F$ is provided, which is preferably an automated method. Also provided by the present invention is a cassette suitable for carrying out the automated method of the invention.

DESCRIPTION OF RELATED ART

Due to its physical and chemical properties, $^{18}F$ is radionuclide a preferred radionuclide for use in positron emission tomography (PET) tracers. The chemical reactions used to incorporate $^{18}F$ into organic molecules can be broadly divided into two categories, namely nucleophilic and electrophilic reactions. For nucleophilic fluorination, [$^{18}F$]-fluoride ion ($^{18}F^-$) is used as the source of $^{18}F$. It is normally obtained as an aqueous solution from the nuclear reaction $^{18}O(p,n)^{18}F$. Once it is made reactive by the addition of a cationic counterion and the removal of water $^{18}F^-$ can be reacted with a compound comprising a suitable leaving group so that 18F becomes incorporated into the compound in place of the leaving group. Suitable leaving groups include Cl, Br, I, tosylate (OTs), mesylate (OMs), nosylate (ONs) and triflate (OTf). The $^{18}F$-labelled compound obtained can either be the final product, or is an $^{18}F$-labelled synthon that is used as a labelling reagent to obtain the final product. An example of such a synthon is $^{18}F$—(CH$_2$)$_x$-LG wherein LG represents a leaving group, which can be used to alkylate thiol, hydroxy, or amine groups in a precursor compound to result in an $^{18}F$-labelled product. In order for the alkylation reaction to proceed successfully, deprotonation of the thiol, hydroxy, or amine group is necessary and as such the reaction is typically carried out in the presence of a base.

$^{18}F$-labelled radiotracers are at present conveniently prepared by means of an automated radiosynthesis apparatus. There are several commercially-available examples of such apparatus. An apparatus such as FASTlab™ (GE Healthcare) comprises a disposable cassette in which the radiochemistry is performed, which is fitted to the apparatus to perform the radiosynthesis. In order for a radiofluorination reaction to be carried out on such an automated synthesis apparatus, it is necessary for each of the reagents to be soluble in order to be transported around the device. In addition, a separate vial is required for each reagent and it is desirable for there to be as few vials as possible in order to simplify the chemistry process, reduce the cost of goods and simplify or minimise the burden of validation and documentation of reagents required for GMP clinical production.

One example of an $^{18}F$-fluoroalkylation reaction to obtain a PET tracer is the following reaction used to obtain $^{18}F$-labelled S-fluoroalkyl diarylguanidines as reported by Robins et al (2010 Bioorg Med Chem Letts; 20: 1749-51):

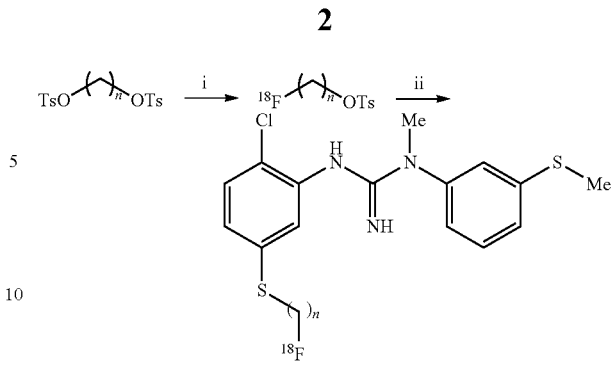

The $^{18}F$-fluoroalkyl tosylate synthons were prepared by reaction in step (i) of the ditosylate starting material with K$^{18}F$/Kryptofix 2.2.2 in acetonitrile at 90° C. for 15 minutes. Although not explicitly stated in the paper, the $^{18}F$-fluoroalkyl tosylate synthons were purified by HPLC prior to use in the next step. The labelled guanidine compounds were obtained in step (ii) by alkylation of the associated thiol precursor compound with the relevant $^{18}F$ fluoroalkyl tosylate synthon in acetonitrile in the presence of the base Cs$_2$CO$_3$. Since Cs$_2$CO$_3$ used in this alkylation reaction is not soluble in acetonitrile, the method for cannot be readily automated.

Another example of an $^{18}F$-fluoroalkylation reaction to obtain a PET tracer is the reaction described by Wang et al (2006 J Radioanalyt Nuc Chem; 270(2): 439-43) used to obtain the $^{18}F$-labeled amino acid O-(2-[$^{18}F$]fluoroethyl)-L-tyrosine ([$^{18}F$]FET):

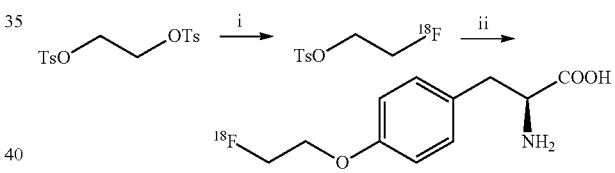

[$^{18}F$]Fluoroethyl tosylate was prepared in step (i) by displacement of a tosyl group from 1,2-bistosyloxyethane by reaction with K $^{18}F$/Kryptofix 2.2.2 in acetonitrile at 90° C. for 10 minutes. The purified [$^{18}F$]fluoroethyl tosylate was then reacted in step (ii) with a solution of L-tyrosine and 10% aqueous NaOH in DMSO (or di-Na-salt of L-tyrosine in DMSO) 20 minutes at 90° C. to obtain [$^{18}F$]FET. In contrast to the method for preparation of $^{18}F$-labelled S-fluoroalkyl diarylguanidines as reported by Robins et al (supra), this method for preparation of [$^{18}F$]FET uses a soluble base in the alkylation reaction. However, the reaction is still not ideal for carrying out on an automated synthesis device that uses a cassette due to the fact that and additional vial is required for the base used for the subsequent fluoroalkylation step.

Lundkvist et al (1997 Nuc Med Biol; 24: 621-7) describe the synthesis of [$^{18}F$]fluoropropyl-β-CIT (β-CIT.(−)-2β-Carbomethoxy-3β-(4-Iodophenyl)tropane) using the [$^{18}F$]fluoropropyl bromide as the labelling reagent. In step (i) [$^{18}F$] fluoropropyl bromide was prepared by a nucleophilic fluorination of 1,3-dibromopropane with [$^{18}F$]potassium Kryptofix complex. [$^{18}F$]Fluoropropyl bromide in dimethyl formamide (DMF) was then used in step (ii) to alkylate nor-β-CIT at 130° C. for 25 minutes to form [$^{18}F$]fluoropropyl-β-CIT:

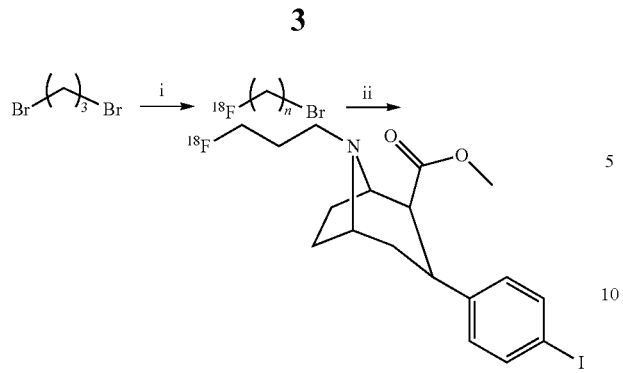

The above method is not ideal for automation since it requires the purification of the synthon via distillation and an additional reagent vial for the base.

There is therefore a need for novel radiofluorination methods that comprise $^{18}$F-fluoroalkylation that overcome the problems associated with the known methods in order to be readily automated. In particular it would be desirable to reduce the number of process steps and to minimise the number of reagents used.

SUMMARY OF THE INVENTION

The present invention provides a method for the synthesis of $^{18}$F-labelled biomolecules, which is amenable to automation. The present invention also provides a cassette for automating the method of the invention. The method of the present invention provides numerous advantages over the prior art methods. It requires one less purification step as compared with known methods. Furthermore, it makes use of a particular reagent in two steps thereby minimises the number of reagent vials required. The chemistry process is thereby simplified, the cost of goods is reduced and the burden of validation and documentation of reagents required for GMP clinical production is minimised.

DETAILED DESCRIPTION OF THE INVENTION

In one aspect the present invention relates to a method for the synthesis of a compound of Formula I:

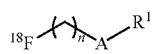

[I]

or a salt or solvate thereof, wherein:

R$^1$-A- is a deprotonated radical of a biological targeting molecule (BTM) of formula R$^1$-A-H wherein A is selected from S, O or NR$^2$ wherein R$^2$ is hydrogen, C$_{1-6}$ alkyl, or C$_{5-12}$ aryl; and, n is an integer of 1-6;

wherein said method comprises:

(i) providing [$^{18}$F]Fluoride trapped on an ion-exchange cartridge;

(ii) eluting the ion-exchange cartridge of step (i) with an aqueous solution comprising a first aliquot of an eluent, wherein said eluent comprises a cationic counterion in a suitable solvent, to obtain a [$^{18}$F]Fluoride eluent;

(iii) reacting a compound of Formula II:

[II]

wherein LG$^1$ and LG$^2$ are the same or different and each represent a leaving group, and n is as defined for Formula I;

in a first solvent with the [$^{18}$F]Fluoride eluent obtained in step (ii) to obtain a compound of Formula III:

[III]

wherein LG$^2$ and n are as defined for Formula II;

(iv) deprotonating a compound of Formula IV:

[IV]

or a protected version thereof, wherein A and R$^1$ are as defined for Formula I;

by addition of a second aliquot of the eluent as defined in step (ii);

(v) reacting the compound of Formula III obtained in step (iii) with said deprotonated compound obtained in step (iv), or a protected version thereof, in a second solvent to obtain said compound of Formula I, or a protected version thereof, wherein said second solvent is an alkanol or an aqueous alkanol, (vi) removing any protecting groups.

A suitable "salt" according to the invention may be selected from: (i) physiologically acceptable acid addition salts such as those derived from mineral acids, for example hydrochloric, hydrobromic, phosphoric, metaphosphoric, nitric and sulphuric acids, and those derived from organic acids, for example tartaric, trifluoroacetic, citric, malic, lactic, fumaric, benzoic, glycollic, gluconic, succinic, methanesulphonic, and para-toluenesulphonic acids; and (ii) physiologically acceptable base salts such as ammonium salts, alkali metal salts (for example those of sodium and potassium), alkaline earth metal salts (for example those of calcium and magnesium), salts with organic bases such as triethanolamine, N-methyl-D-glucamine, piperidine, pyridine, piperazine, and morpholine, and salts with amino acids such as arginine and lysine.

A suitable "solvate" according to the invention may be formed with ethanol, water, saline, physiological buffer and glycol.

The term "alkyl" used either alone or as part of another group is defined as any straight, branched or cyclic, saturated or unsaturated C$_n$H$_{2n+1}$ group.

The term "aryl" used either alone or as part of another group is defined as any C$_{6-14}$ molecular fragment or group which is derived from a monocyclic or polycyclic aromatic hydrocarbon, or a monocyclic or polycyclic heteroaromatic hydrocarbon.

The term "biological targeting moiety" (BTM) is meant a compound which, after administration, is taken up selectively or localises at a particular site of the mammalian body in vivo. Such sites may for example be implicated in a particular disease state or be indicative of how an organ or metabolic process is functioning. The BTM may be of synthetic or natural origin, but is preferably synthetic.

The term "synthetic" has its conventional meaning, i.e. man-made as opposed to being isolated from natural sources e.g. from the mammalian body. Such compounds have the advantage that their manufacture and impurity profile can be fully controlled. The molecular weight of the BTM is preferably up to 3,000 Daltons, more preferably 200 to 2,500 Daltons, most preferably 300 to 2,000 Daltons, with 400 to 1,500 Daltons being especially preferred.

Preferably the BTM is an enzyme substrate, enzyme antagonist, enzyme agonist, enzyme inhibitor or receptor-binding compound, in particular a non-peptide, and preferably is synthetic. By the term "non-peptide" is meant a compound which does not comprise any peptide bonds, i.e. an amide bond between two amino acid residues. When the BTM is an enzyme substrate, enzyme antagonist, enzyme agonist or enzyme inhibitor, preferred such biological targeting molecules of the present invention are synthetic, drug-like small molecules i.e. pharmaceutical molecules. Non-limiting examples of particular such biological targeting molecules are described in more detail hereunder.

A suitable "ion-exchange cartridge" in the context of the present invention is a solid-phase extraction (SPE) cartridge that retains $^{18}F^-$ and allows $^{18}O$ to pass through when an aqueous solution from the nuclear reaction $^{18}O(p,n)^{18}F$ is passed through. Preferably, said ion-exchange cartridge is an anion exchange cartridge, most preferably a quaternary methylammonium (QMA) cartridge.

A "cationic counterion" in the context of the present invention is a positively-charged counterion that acts to improve the reactivity of [$^{18}F$]Fluoride when combined therewith. A suitable cationic counterion for use in the method of the present invention may be a large but soft metal ion such as rubidium or caesium, a metal complex of a cryptand or a tetraalkylammonium salt. A preferred cationic counterion is a metal complex of a cryptand or a tetraalkylammonium salt. A preferred metal in a metal complex of a cryptand is potassium. A preferred cryptand in a metal complex of a cryptand is Kryptofix 222. A preferred tetraalkylammonium salt is selected from $R_4N^+$ wherein R is ethyl, methyl or butyl. The "suitable solvent" for the eluent is an alkanol, and is preferably ethanol or methanol, most preferably ethanol.

The "aqueous solution comprising a first aliquot of an eluent comprising a cationic counterion" refers to a solution comprising an aliquot of said eluent made up with water. This aqueous solution is used as a phase transfer catalyst to improve solubility and nucleophilicity of [$^{18}F$]fluoride. In the eluting step said aqueous solution is passed through the ion-exchange cartridge, bringing with it the [$^{18}F$]fluoride to result in an "[$^{18}F$]eluent" comprising [$^{18}F$]fluoride in said aqueous solution.

Said [$^{18}F$]Fluoride eluent may be dried before subsequent use, suitably by evaporation of water to result in anhydrous [$^{18}F$]Fluoride eluent. This drying step is for example carried out by application of heat and use of a solvent such as acetonitrile to provide a lower boiling azeotrope.

The term "leaving group" refers to a molecular fragment that departs with a pair of electrons in heterolytic bond cleavage. A suitable leaving group can be a halo, e.g. selected from chloro, iodo, or bromo. A preferred suitable leaving group can be an aryl or alkyl sulphonate, for example, tosylate, triflate, nosylate or mesylate.

The "first solvent" used in step (iii) of the method of the invention is suitably one in which both the compound of Formula II and the dried [$^{18}F$]fluoride eluent are soluble. Generally, a dipolar aprotic solvent is suitable, preferably an alkyl nitrile, most preferably acetonitrile.

As in the case of the [$^{18}F$]Fluoride eluent, the compound of Formula III may be dried before subsequent use to remove the solvent, which can be particularly important when the solvent is an alkyl nitrile such as acetonitrile. The present inventors have observed that the presence of such a solvent in the alkylation reaction mixture can lead to the generation of acetyl impurities that are difficult to remove from the final product. For the compound of Formula III, drying is suitably carried out by application of heat and/or vacuum and/or use of gas flow (typically nitrogen).

The term "deprotonating" refers to the removal of a proton ($H^+$) from a molecule. The step of deprotonating the compound of Formula IV is carried out using a second aliquot of the eluent as defined in step (ii) where in this part of the process the eluent acts as soluble base.

Suitable "protecting groups" and methods for "removing protecting groups" are well known to those skilled in the art. The use of protecting groups is described in 'Protective Groups in Organic Synthesis', by Greene and Wuts (Fourth Edition, John Wiley & Sons, 2007). The step of removing these protecting groups, if present, is preferably carried out after the alkylation step.

The second solvent used in step (v) of the method of the invention an alkanol or an aqueous alkanol, wherein the term "alkanol" is taken to mean a simple aliphatic alcohol. An "aqueous alkanol" consists of water and an alkanol. Suitably said second solvent does not comprise any solvents apart from water and alkanol, and in particular does not comprise acetonitrile. Suitable alkanols in the context of the present invention include methanol, ethanol and propanol, with ethanol being most preferred.

In Formulae II and III, n is preferably 1-4, most preferably 1-3 and most especially preferably 1-2.

Reacting step (v) which is the alkylation step may be carried out either at room temperature or at higher temperatures (typically 90-130° C.). In a preferred embodiment, the compound of Formula III from step (iii) is used directly in the alkylation step (v). That is, no purification step is carried out on the crude reaction product of step (iii) before carrying out step (v), which makes the method relatively simple and therefore even more amenable to automation. It is also envisaged that reacting step (v) can be followed by a purification step to obtain substantially pure compound of Formula I. Examples of suitable purification methods are solid-phase extraction (SPE) and high-performance liquid chromatography (HPLC).

An additional advantage of the present method over known methods is that purification of the compound of Formula I can be made easier by avoiding generation in the presence of acetonitrile of acetyl impurities. For example, the present inventors found that in the synthesis of 3-(2-chloro-5-((2-[$^{18}F$]fluoroethyl)thio)phenyl)-1-methyl-1-(3-(methylthio) phenyl)guanidine from 3-(2-chloro-5-((2-hydroxyethyl)thio) phenyl)-1-methyl-1-(3-(methylthio)phenyl)guanidine, an acetyl impurity was formed that proved difficult to separate. The scheme below illustrates the proposed mechanism by which this impurity is formed:

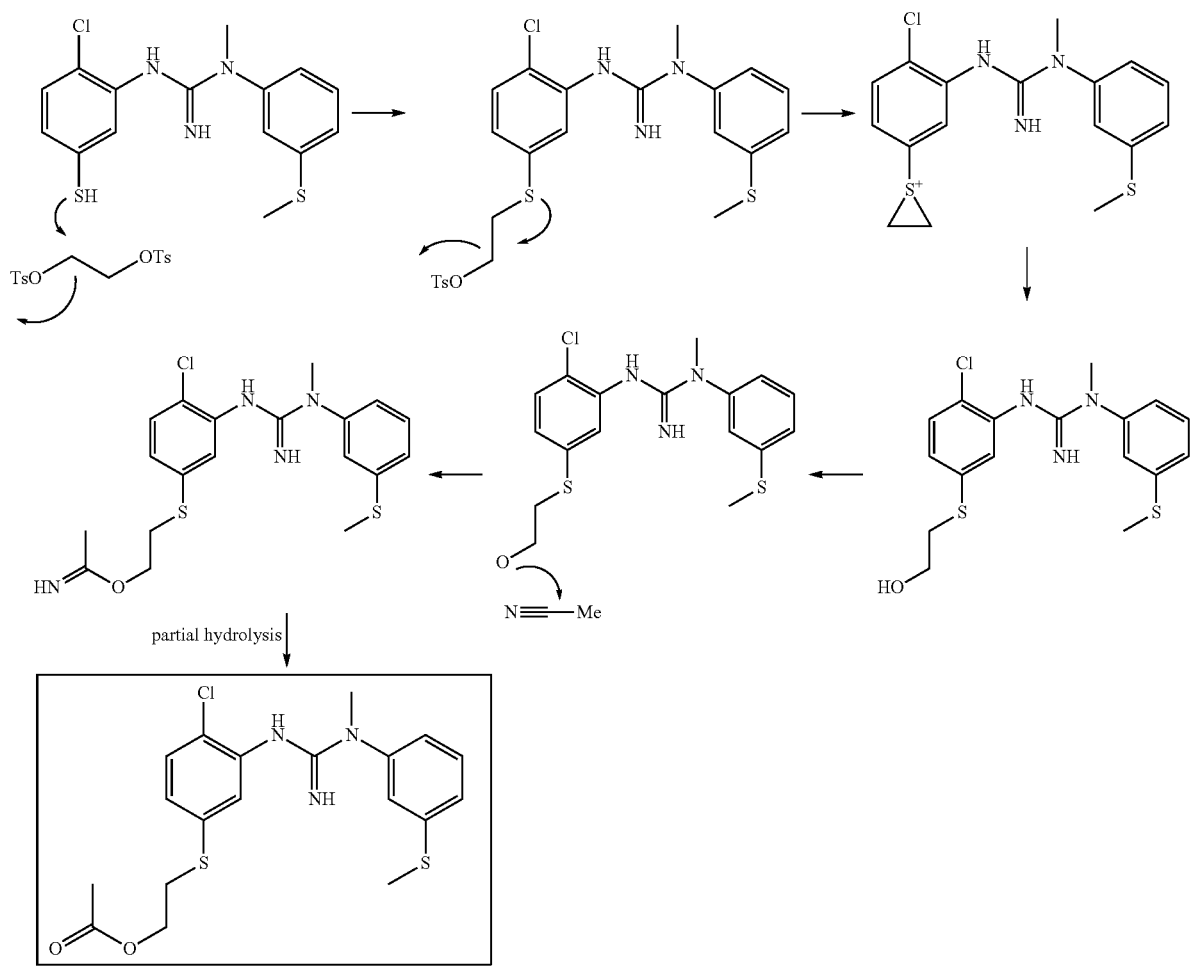

Use of an alkanol in place of acetonitrile in the [$^{18}$F]fluoroalkylation step avoids the production of this acetyl impurity.

The method reported by Robins et al (2010 Bioorg Med Chem Letts; 20: 1749-51) for the synthesis of $^{18}$F-labelled S-fluoroalkyl diarylguanidines comprises [$^{18}$F]fluoroalkylation of a thiol group. The method can be readily adapted to be a method of the present invention.

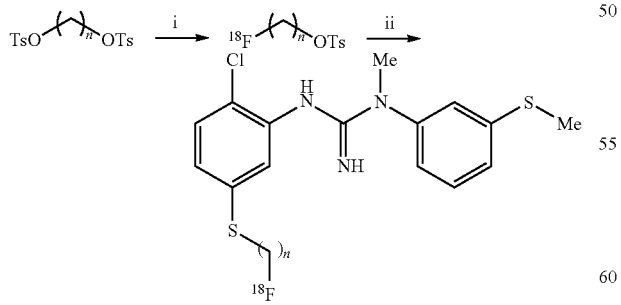

Firstly, the [$^{18}$F]fluoroalkylation step (ii) is carried out in an aqueous alkanol rather than acetonitrile. Also, there is no requirement to purify the [$^{18}$F]fluoroethyltosylate in order to avoid the acetyl impurity. In addition, an aliquot of the solution the eluent of $K_2CO_3$ and Kryptofix 222 where the complex K(Kryptofix)$_2$CO$_3$ is used to make "reactive" [$^{18}$F][K(Kryptofix)]F for use in step (i) is used in place of Cs$_2$CO$_3$ in step (ii) where the complex K(Kryptofix)$_2$CO$_3$ is used as a base.

Accordingly, an example of a preferred BTM of formula $R^1$-A-H in the method of the present invention is a compound of Formula Ia:

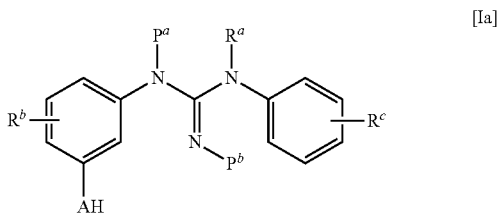

wherein A is as defined in claim 1, and.

$R^a$ is selected from hydrogen or $C_{1-4}$ alkyl;

$R^b$ is halo;

$R^c$ is selected from halo, $C_{1-4}$ alkylthio, or $C_{1-4}$ alkyl; and, $P^a$ and $P^b$ are independently hydrogen or an amine protecting group, preferably hydrogen.

Preferably, said BTM of Formula Ia is a compound of Formula Ib:

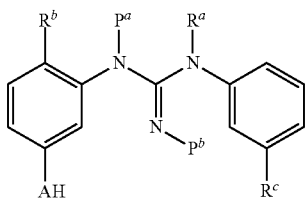

wherein A, $R^{a-c}$, $P^a$ and $P^b$ are as defined for Formula Ia.
$R^a$ is preferably $C_{1-4}$ alkyl and most preferably methyl.
$R^b$ is preferably chloro.
$R^c$ is preferably alkylthio, and most preferably methylthio.
A is preferably S.
For any particular compound of Formula Ia or Formula Ib:
$R^a$ is $C_{1-4}$ alkyl and is most preferably methyl;
$R^b$ group is chloro;
$R^c$ group is alkylthio, and is most preferably methylthio;
A is S.
A particularly preferred compound of Formula Ib is the following compound.

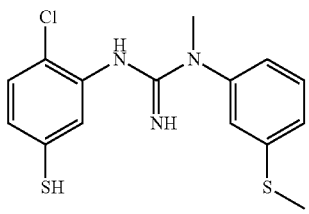 [SMILES: CSc1cccc(N(C)C(=N)Nc2cc(S)ccc2Cl)c1]

The above-defined compounds of Formulae Ia and Ib may be prepared by use or straightforward adaptation of the methods described variously in WO 94/27591, WO 2004/007440, WO 2006/136846, Hu et al (J Med Chem, 1997; 40: 4281-9), Zhao et al (J Label Compd Radiopharm, 2006; 49: 163-70) and Robins et al (Bioorganic and Medicinal Chemistry Letters, 2010; 20 (5): 1749-51).

The skilled person will appreciate that the method of the present invention may be applied to the preparation of a range of $^{18}$F-labelled compounds. For instance, a non-limiting example of a known method that can be adapted in a straightforward manner to result in a method of the present invention is the method comprising [$^{18}$F]fluoroalkylation of a phenol described by Wang et al (2006 J Radioanalyt Nuc Chem; 270(2): 439-43) to obtain the $^{18}$F-labeled amino acid O-(2-[$^{18}$F]fluoroethyl)-L-tyrosine ([$^{18}$F]FET):

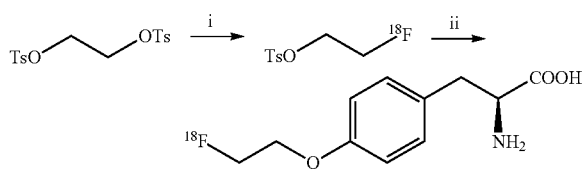

[$^{18}$F]Fluoroethyl tosylate obtained in step (i) can be reacted in step (ii) (without needing to first be purified) with a solution of L-tyrosine in an aqueous alkanol (rather than DMSO) which has been treated with an aliquot of the solution of $K_2CO_3$ and Kryptofix 222 (rather than NaOH) previously used in the method to make reactive [$^{18}$F][K(Kryptofix)]F for use in step (i).

Accordingly, another example of a preferred BTM of formula $R^1$-A-H in the method of the present invention is the following compound.

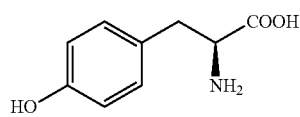 [SMILES: N[C@@H](Cc1ccc(O)cc1)C(=O)O]

Another non-limiting example of a known method that may be easily adapted is the method described by Lundkvist et al (1997 Nuc Med Biol; 24: 621-7) for the synthesis of [$^{18}$F]fluoropropyl-β-CIT (β-CIT: (−)-2β-Carbomethoxy-3β-(4-iodophenyl)tropane) a secondary amine is alkylated using [$^{18}$F]fluoropropyl bromide:

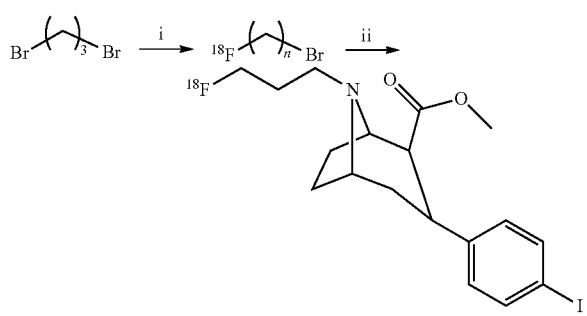

This method can be readily converted to be a method of the present invention by carrying out step (ii) in an aqueous alkanol solution using an aliquot of $K_2CO_3$ and Kryptofix 222 (with acetonitrile removed) used to make reactive [$^{18}$F][K(Kryptofix)]F for use in step (i).

Accordingly, another example of a preferred BTM of formula $R^1$-A-H in the method of the present invention is the following compound:

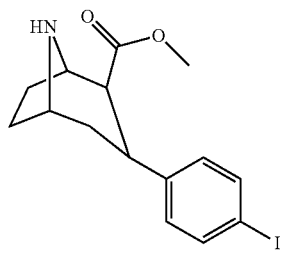 [SMILES: COC(=O)C1C2CCC(CC1c1ccc(I)cc1)N2]

The above-described compounds merely provide illustrations of how the method of the present invention may be applied. It will be clearly appreciated by the skilled person that the method of the present invention can also be applied to achieve similar advantages to any reaction that comprises (i) synthesis of an [$^{18}$F]fluoroalkyl labelling reagent using [$^{18}$F] fluoride as the source of is F, and (ii) [$^{18}$F]fluoroalkylation of a thiol, hydroxy or amine functionality in a precursor compound.

The method of the present invention has the advantage that it does not require purification of the compound of Formula III for use in the alkylation step, and also that it minimises the number of reagent vials used since the eluent reagent vial would be used twice—once as phase transfer catalyst and once as a base.

The method of the present invention is particularly amenable to automation as compared to known methods. Automation may be carried out on an automated radiosynthesis apparatus. There are several commercially-available examples of such apparatus, including Tracerlab MX™ and FASTlab™ (GE Healthcare), FDGPlus Synthesizer (Bioscan) and Synthera® (IBA). Such apparatus may comprise a "cassette", often disposable, in which the radiochemistry is performed, which is fitted to the apparatus in order to perform a radiosynthesis. The cassette normally includes fluid pathways, a reaction vessel, and ports for receiving reagent vials as well as any solid-phase extraction cartridges used in post-radiosynthetic clean up steps. As the method of the present invention does not require purification of the first crude reaction product, and as the second crude reaction product is relatively easy to purify, the method of the present invention is amenable to automation. Therefore, in a preferred embodiment, the method of the present invention is automated, most preferably by means of a cassette on an automated radiosynthesis apparatus.

The present invention provides in another aspect a cassette for the automated synthesis of the compound of Formula I as defined herein wherein said cassette comprises:
  (i) a first vessel containing eluent as defined in step (ii) of Claim 1;
  (ii) a second vessel containing a compound of Formula II as defined in step (iii) of Claim 1;
  (iii) a third vessel containing a compound of Formula IV as defined in step (iv) of Claim 1;
  (iv) a fourth vessel in which reacting steps (iii) and (v) as defined in Claim 1 are carried out; and,
  (v) an ion-exchange cartridge for trapping [$^{18}$F]fluoride.

Any indications for the cassette of the present invention that have been defined above for the method of the present invention are as suitably and preferably defined herein for the method of the invention.

The term "vessel" is taken to mean a reagent vial suitable for placing in a position on a cassette to be used with an automated synthesis cartridge.

Depending on the stability of the compound of Formula II and of the compound of Formula IV, either of the vials containing these compounds may optionally be provided separately to the cassette in order to be stored, e.g. under refrigeration or frozen, until use for carrying out the method of the invention when the vial is brought to room temperature and then included in the cassette. The compounds of Formulae II and IV may each be provided in their respective vial either in solution or in dried, e.g. lyophilised, form to be reconstituted before use with the appropriate solvent set out above for the method of the invention.

Additional vessels may be present specific to the chemistry/BTM synthesis e.g. vials for solvents for deprotection, purification, formulation, reformulation. Additional cartridges (SPE) may also be present for purification and/or re-formulation. There may also be a connection line from the cassette to a HPLC unit if HPLC purification is required, and there may be a connection line from the "HPLC cut vial" to the cassette if there is a requirement for solvent reformulation post purification.

The reagents, solvents and other consumables required for the automated synthesis may also be included together with a data medium, such as a compact disc carrying software, which allows the automated synthesiser to be operated in a way to meet the end user's requirements for concentration, volumes, time of delivery etc.

BRIEF DESCRIPTION OF THE EXAMPLES

Example 1 describes the automated synthesis of 3-(2-chloro-5-((2-[$^{18}$F]fluoroethyl)thio)phenyl)-1-methyl-1-(3-(methylthio)phenyl)guanidine using the method of the present invention.

Example 2 describes an experiment comparing FASTab™ synthesis of 3-(2-chloro-5-((2-[$^{18}$F]fluoroethyl)thio)phenyl)-1-methyl-1-(3-(methylthio)phenyl)guanidine using ethanol or acetonitrile as the solvent.

LIST OF ABBREVIATIONS USED IN THE EXAMPLES

EtOH ethanol
HPLC high performance liquid chromatography
$K_{222}$ Kryptofix 2.2.2
MeCN acetonitrile
QMA quaternary methylammonium
SPE solid phase extraction
TsO tosylate

EXAMPLES

Example 1

FASTlab™ Synthesis of 3-(2-chloro-5-((2-[$^{18}$F]fluoroethyl)thio)phenyl)-1-methyl-1-(3-(methylthio)phenyl)guanidine A cassette for use with a FASTlab™ synthesiser comprised the following vials:

| Vial number | Vial name | Composition |
|---|---|---|
| 1 | Eluent | $K_{222}$ = 53 mg/mL; $K_2CO_3$ 9.5 mg/mL Solvent: (12.5% water, 87.5% EtOH) |
| 2 | TsO(CH$_2$)$_2$OTs | Ethylene ditosylate (4.0 mg) MeCN (1.6 mL) |
| 3 | EtOH | EtOH (4.0 mL) |
| 4 | HCl | 0.1M HCl (4 ml) |
| 5 | Precursor | Precursor* (15 mg) EtOH (1.8 mL)) |

*3-(2-chloro-5-((2-hydroxyethyl)thio)phenyl)-1-methyl-1-(3-(methylthio)phenyl)guanidine The cassette is also illustrated in FIG. 1.

1(i) Transfer of [$^{18}$F]Fluoride to Cassette

[$^{18}$F]Fluoride was supplied from GE Healthcare on a GE PETrace cylcotron. The initial activity was transferred via the activity inlet of the FASTlab™ cassette using vacuum.

1(ii) Trapping [$^{18}$F]Fluoride on the QMA

The activity was transferred from the activity inlet to the (pre-treated) QMA cartridge where the [$^{18}$F] was trapped and the water passed through to the $^{18}$O water recovery vial, using a combination of N$_2$ to push and vacuum to pull.

1(iii) Elution of [$^{18}$F]Fluoride Off the QMA

70 μL of the eluent vial (K$_{222}$, K$_2$CO$_3$) was removed from the eluent vial using the 1 mL syringe. 550 μL of water was then withdrawn from the water bag and added to the eluent in the 1 mL syringe. The [$^{18}$F]fluoride trapped on the QMA cartridge was then eluted into the reaction vessel using the eluent/water solution in the 1 mL syringe and a vacuum applied to the reaction vessel to draw the solution through the QMA cartridge.

1(iv) Drying [¹⁸F]Fluoride

The [¹⁸F]fluoride and eluent solution was dried for 20 minutes by heating (100° C.) and a combination of nitrogen and vacuum were used to remove the evaporated solvent and water from the reaction vessel to a waste collection vessel.

1(v) Radiosynthesis of [¹⁸F]-fluoroethyltosylate 1 mL of the ethylene ditosylate solution (2.5 mg per mL of MeCN) was removed from the vial using the centre (5 ml) syringe and dispensed into the reaction vessel containing the dried [¹⁸F]fluoride/K222/K₂CO₃ (reactive [¹⁸F][K(Kryptofix)]F). The reaction vessel was then sealed and the reaction carried out by heating for 15 minutes at 86° C.

1(vi) Removal of Solvent from the [¹⁸F]-Fluoroethyltosylate

The crude [¹⁸F]-fluoroethyltosylate/ethylene ditosylate solution was dried for 10 minutes by heating (80° C.) and a combination of nitrogen and vacuum was used to remove the evaporated solvent from the reaction vessel to a waste collection vessel.

1(vii) Introduction of 500 μL of Eluent to Precursor Vial

500 μL of eluent vial (K₂₂₂, K₂CO₃) was removed from the eluent vial and added into the precursor vial using the 1 mL syringe. The solution was held for 1 minute.

1(viii) Introduction of Precursor to Reaction Vessel 10 mg (26 μmol) of precursor (3-(2-chloro-5-((2-hydroxyethyl)thio)phenyl)-1-methyl-1-(3-(methylthio)phenyl) guanidine) in 1.5 mL of ethanol was removed from the vial by creating a vacuum in the reaction vessel.

1(ix) Alkylation of Precursor

The reaction vessel was then sealed and the alkylation carried out by initially heating for 2 minutes at 80° C., then 13 minutes at 100° C.

1(x) Loop Flush Out with Water

A total of 10 mL water was removed from the water bag using the centre (5 ml) syringe and sent through the HPLC loop in two syringe movements.

1(xi) Quench Reaction, and Transfer Out of FASTlab to HPLC Loop 2 mL water was added to the reaction vessel from the water bag using the centre 5 mL syringe. 1 mL 0.1 M HCl was added to the reaction vessel from the vial using the centre 5 mL syringe. This was then withdrawn from the reaction vessel using the same syringe and transferred from the cassette to the HPLC loop, followed by a purge of the line and cassette fluid path with nitrogen to clear any residual solution to the HPLC loop.

1(xii) HPLC Purification and SPE Formulation

The following HPLC method was used:

| | |
|---|---|
| 0-60 mins | 40% (B) |
| Column | ACE C18 100 × 10 mm 5 μm |
| Mobile phase | Mobile phase A (pump A): Acetonitrile (pump B) |
| Loop Size | 10 ml |
| Pump speed | 3 ml/min |
| Wavelength | 254 nm |
| Mobile Phase A. | 0.8% TEA [TEA (8 ml) and H2O (992 ml)], pH adj. to ca. 7.5 with 85% H3PO4 (ca. 2.1 ml) |

The HPLC run was controlled from the HPLC software until the cut was performed.

The HPLC cut was transferred back to the FASTlab using the right hand (5 ml) syringe to draw the cut back on to the cassette then add to the dilution water bag. The diluted HPLC cut (>100 mL) was loaded on to a tC18+ SPE cartridge by applying a vacuum for 11 minutes to draw the full content of the water bag through the cartridge to a waste collection vessel. The SPE cartridge was eluted with 1 mL ethanol from the vial using the right hand 5 mL syringe into a vial containing 14 mL saline containing 1.5 mg ascorbic acid.

In summary, the following were observed.

| | |
|---|---|
| Average yield (MBq) (starting from 37 GBq of [¹⁸F]fluoride) | 3177 |
| Average RCP (%) | 97 |
| Average Specific Activity (GBq/μmole0029 | 581 |
| Number of production runs | 23 |

Example 2

Figure 2:
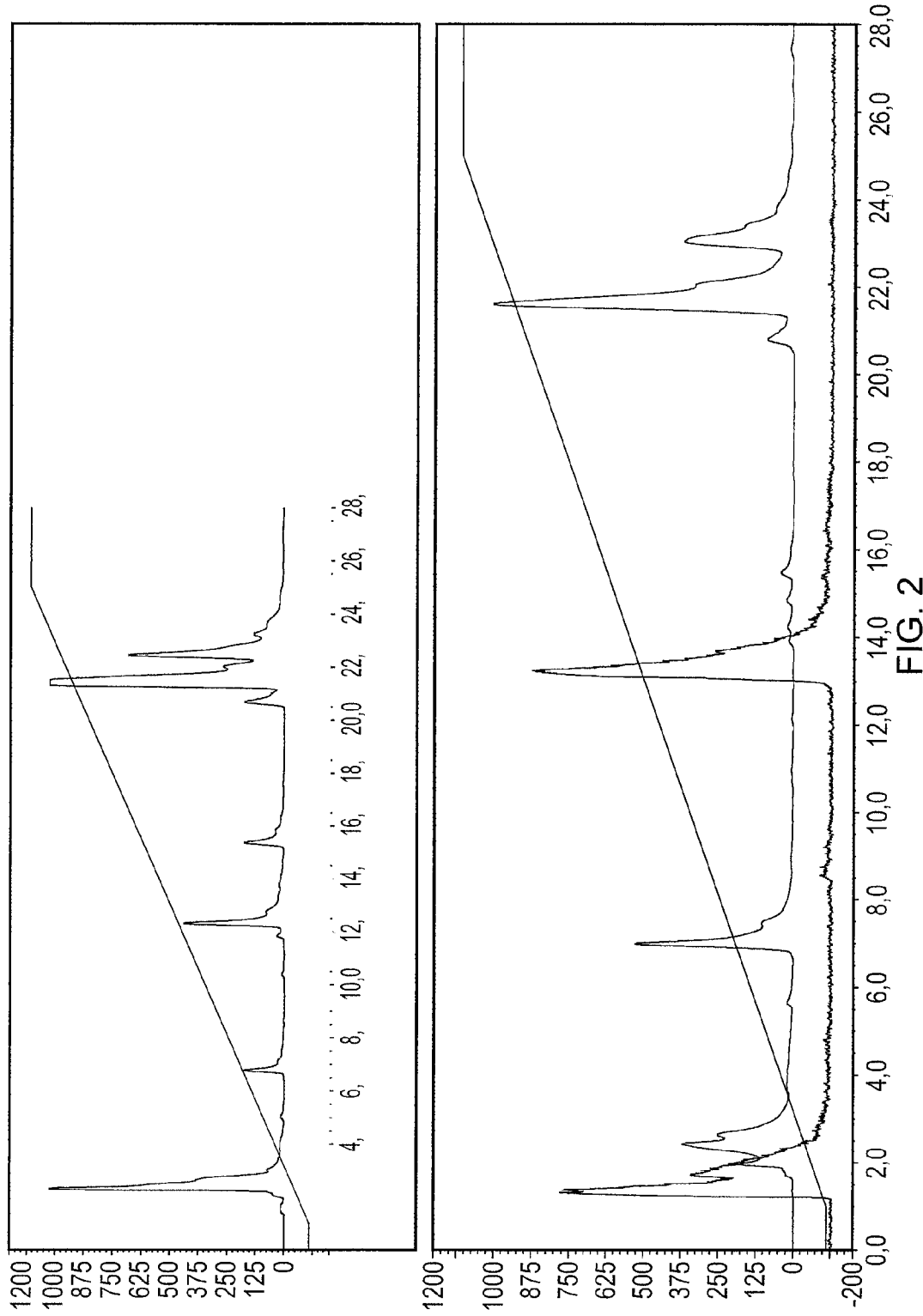

Comparison of FASTlab™ Synthesis of 3-(2-chloro-5-((2-[¹⁸F]fluoroethyl)thio)phenyl)-1-methyl-1-(3-(methylthio)phenyl)guanidine using Ethanol or Acetonitrile as the solvent The process described in Example 1 was carried out up to step 1(xi) but wherein the following step was analytical HPLC using the following method:

Mobile Phase A: 0.8% TEA (8 mL TEA and 992 mL H₂O), pH adj. to ca. 7.5 with 85% H₃PO₄ (ca. 2.1 mL)
Mobile phase B: MeCN
0-1 mm 40% B; 1-25 min 40-95% B
HPLC column: Luna C18 (150×4.6 mm)
Flow rate: 1 mL/min In addition, the same process was carried out wherein acetonitrile was used as the solvent in place of ethanol. FIG. 2 compares the synthesis wherein acetonitrile (top) was used in place of ethanol (bottom) as the solvent. It can be clearly seen that the acetyl chemical impurity that elutes around 12 minutes (with product eluting just afterwards) is not formed when acetonitrile has been removed from the alkylation step.

What is claimed is:

1. A method for the synthesis of a compound of Formula I:

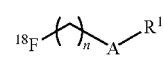

or a salt or solvate thereof, wherein:

R¹-A- is a deprotonated radical of a biological targeting molecule (BTM) of formula R¹-A-H wherein A is selected from S, O or NR² wherein R² is hydrogen, C₁₋₆ alkyl, or C₅₋₁₂ aryl; and, n is an integer of 1-6;

wherein said method comprises:

(i) providing [¹⁸F]Fluoride trapped on an ion-exchange cartridge;

(ii) eluting the ion-exchange cartridge of step (i) with an aqueous solution comprising a first aliquot of an eluent, wherein said eluent comprises a cationic counterion in a suitable solvent, to obtain a [¹⁸F]Fluoride eluent;

(iii) reacting a compound of Formula II:

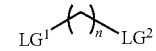

wherein LG¹ and LG² are the same or different and each represent a leaving group, and n is as defined for Formula I;

in a first solvent with the [¹⁸F]Fluoride eluent obtained in step (ii) to obtain a compound of Formula III:

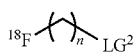

wherein LG² and n are as defined for Formula II;

(iv) deprotonating a compound of Formula IV:

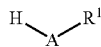

or a protected version thereof, wherein A and R¹ are as defined for Formula I;
by addition of a second aliquot of the eluent as defined in step (ii);

(v) reacting the compound of Formula III obtained in step (iii) with said deprotonated compound obtained in step (iv), or a protected version thereof, in a second solvent to obtain said compound of Formula I, or a protected version thereof, wherein said second solvent is an alkanol or an aqueous alkanol;

(vi) removing any protecting groups.

2. The method as defined in claim 1 wherein said ion-exchange cartridge is an anion exchange cartridge.

3. The method as defined in claim 2 wherein said anion exchange cartridge is a quaternary methylammonium (QMA) cartridge.

4. The method as defined in claim 1 wherein said cationic counterion is a metal complex of a cryptand.

5. The method as defined in claim 1 wherein said metal complex of a cryptand is a potassium salt of Kryptofix 222.

6. The method as defined in claim 1 wherein LG¹ and LG² of Formula II are independently selected from halo or an aryl or alkyl sulphonate.

7. The method as defined in claim 6 wherein LG¹ and LG² are independently a halo selected from chloro, iodo and bromo.

8. The method as defined in claim 6 wherein LG¹ and LG² are independently an aryl or alkyl sulphonate selected from tosylate, triflate and mesylate.

9. The method as defined in claim 1 wherein said first solvent is an alkyl nitrile.

10. The method as defined in claim 9 wherein said alkyl nitrile is acetonitrile.

11. The method as defined in claim 1 wherein said alkanol is ethanol.

12. The method as defined in claim 1 which is automated.

13. The method as defined in claim 1 wherein said BTM is an enzyme substrate, enzyme antagonist, enzyme agonist, enzyme inhibitor or receptor-binding compound.

14. The method as defined in claim 13 wherein said BTM is a receptor-binding compound.

15. The method as defined in claim 13 wherein said BTM is a non-peptide.

16. The method as defined in claim 13 wherein said BTM is synthetic.

17. The method as defined in claim 1 wherein said BTM is a compound of Formula Ia:

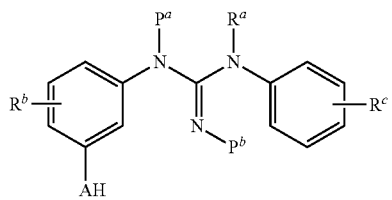

wherein A is as defined in claim 1, and:
$R^a$ is selected from hydrogen or $C_{1-4}$ alkyl;
$R^b$ is halo;
$R^c$ is selected from halo, $C_{1-4}$ alkylthio, or $C_{1-4}$ alkyl; and,
$P^a$ and $P^b$ are independently hydrogen or an amine protecting group.

18. The method as defined in claim 17 wherein BTM is a compound of Formula Ib:

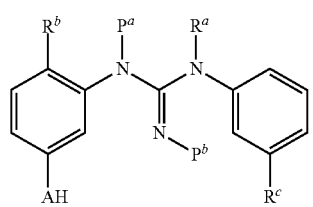

wherein A, $R^{a-c}$, $P^a$ and $P^b$ are as defined for Formula Ia.

19. The method as defined in claim 1 wherein said BTM is the following compound:

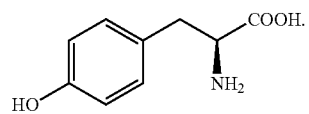 [SMILES: N[C@@H](Cc1ccc(O)cc1)C(=O)O]

20. The method as defined in claim 1 wherein said BTM is the following compound:

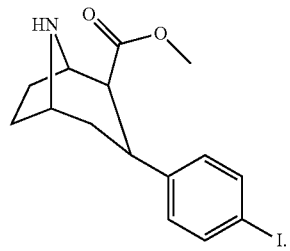 [SMILES: COC(=O)C1C2CCC(CC1c1ccc(I)cc1)N2]

21. A cassette for carrying out the method as defined in claim 1 comprising:
(i) a first vessel containing eluent as defined in step (ii) of claim 1;
(ii) a second vessel containing a compound of Formula II as defined in step (iii) of claim 1;
(iii) a third vessel containing a compound of Formula IV as defined in step (iv) of claim 1;
(iv) a fourth vessel in which reacting steps (iii) and (v) as defined in claim 1 are carried out; and,
(v) an ion-exchange cartridge for trapping [¹⁸F]fluoride.

* * * * *